US005772999A

United States Patent [19]
Greenblatt et al.

[11] Patent Number: 5,772,999
[45] Date of Patent: Jun. 30, 1998

[54] METHOD OF PREVENTING, COUNTERING, OR REDUCING NSAID-INDUCED GASTROINTESTINAL DAMAGE BY ADMINISTERING MILK OR EGG PRODUCTS FROM HYPERIMMUNIZED ANIMALS

[75] Inventors: Hellen Chaya Greenblatt, Wilmington, Del.; Orn Adalsteinsson, Kennett Square, Pa.; David Alan Brodie, East Windsor, N.J.; Sandra G. Fitzpatrick-McElligott, Rose Valley, Pa.

[73] Assignee: DCV Biologics, L.P., Wilmington, Del.

[21] Appl. No.: 688,576

[22] Filed: Jul. 30, 1996

[51] Int. Cl.[6] ................................. A61K 39/395
[52] U.S. Cl. ..................... 424/187.1; 424/158.1
[58] Field of Search .................. 424/157.1, 158.1

[56] References Cited

U.S. PATENT DOCUMENTS

| | | | |
|---|---|---|---|
| 4,284,623 | 8/1981 | Beck | 424/85 |
| 4,550,019 | 10/1985 | Polson | 424/85 |
| 5,106,618 | 4/1992 | Beck et al. | 424/85.8 |
| 5,215,746 | 6/1993 | Stolle et al. | 424/92 |
| 5,352,462 | 10/1994 | Beck | 424/278.1 |
| 5,367,054 | 11/1994 | Lee | 530/359 |
| 5,420,253 | 5/1995 | Emery et al. | 530/423 |

OTHER PUBLICATIONS

Itescu S., "Rheumatic aspects of acquired immunodeficiency syndrome", Current Opinion in Rheumatology 8 (4) : 346–53 (1996).

Bourinbaiar et al., "The non–steroidal anti–inflammatory drug, indomethacin, as an inhibitor of HIV replication", FEBS Letters 360 (1) : 85–8 (1995).

Ebina T. Et Al., Microbiology & Immunology 34(7):617–29 (1990).

*Primary Examiner*—Sandra E. Saucier

[57] ABSTRACT

A method of preventing, countering or reducing chronic gastrointestinal disorders or NSAID-induced gastrointestinal damage in a subject suffering from such ailments. The method comprises hyperimmunizing an egg-producing and/or milk-producing animal and administering an effective amount of hyperimmunized egg product, hyperimmunized milk product or mixtures thereof to the subject.

14 Claims, No Drawings

5,772,999

METHOD OF PREVENTING, COUNTERING, OR REDUCING NSAID-INDUCED GASTROINTESTINAL DAMAGE BY ADMINISTERING MILK OR EGG PRODUCTS FROM HYPERIMMUNIZED ANIMALS

FIELD OF THE INVENTION

This invention relates to a method for treating gastrointestinal damage. More particularly, this invention relates to a method of preventing, countering, or reducing chronic gastrointestinal disorders as well as nonsteroidal, anti-inflammatory drug-induced gastrointestinal damage using a natural food product.

BACKGROUND OF THE INVENTION

Nonsteroidal, anti-inflammatory drugs, generally referred to as NSAIDs, have strong anti-inflammatory, antipyretic, and analgesic properties, and are an effective treatment for inflammatory diseases, such as rheumatoid arthritis, osteoarthritis, ankylosing spondylitis, bursitis, and tendinitis. This large class of drugs includes drugs such as: indomethacin, aspirin, naproxen, ibuprofen and diclofenac. All of these compounds afford great relief to the more than 50 million individuals suffering from inflammatory diseases in the United States. In addition to their effectiveness against joint related inflammatory diseases, NSAIDs may prevent or reduce the risk of other diseases that may be associated with inflammation, such as multiple sclerosis, Alzheimer's disease, and Parkinson's disease.

However, patients treated with NSAIDs on a long term basis often experience serious side effects. Up to 50% of patients receiving conventional therapeutic dosages of NSAIDs experience gastrointestinal damage, and about 20% must discontinue use due to these side effects. The side effects include anorexia, nausea and abdominal pain at usual dosages. At higher dosages, side effects include single or multiple ulcerations of the upper gastrointestinal tract that may result in hemorrhaging. In some cases, for example when perforations occur, these side effects may result in fatalities. In the United States, 6,000 deaths per year are thought to be caused by NSAID-related gastrointestinal damage.

Thus, physicians prescribing non-steroidal, anti-inflammatory drugs for their patients are faced with a serious dilemma. They can use NSAIDs to reduce joint pain and increase mobility of their patients (e.g., in arthritis), but as a result of this type of drug therapy, risk that their patients may develop intestinal ulcers. The causes of intestinal ulceration produced by NSAIDs are multifactorial. For example, due to the way drugs circulate in the body, they often concentrate in the bile. The high concentration of NSAIDs in the bile may cause direct contact irritation and result in damage of the intestinal mucosal surface. Also, changes in inflammatory mediators in the mucosa and intestinal lumen, alterations in blood flow and bacterial growth have been implicated.

Regimens of therapy that inhibit NSAID induced gastrointestinal damage include antacids (acid neutralization), and cimetidine, ranitidine and famotidine (acid secretion inhibition). Although high dosages of steroids and antibiotics have provided some protection from NSAID damage of the intestinal mucosa, at the present time there is no drug of choice for prevention of NSAID induced enteritis.

Some non NSAID-induced gastrointestinal disorders include those that are chronic, such as Inflammatory Bowel Disease. Inflammatory Bowel Disease is a serious, progressive condition that affects the gastrointestinal tract and causes a significant decrease in the quality of life for those suffering from this disease. This condition presents itself in the forms of Crohn's disease and ulcerative colitis. The symptoms are malabsorption, diarrhea, abdominal pain, anemia, weight loss and intestinal wall lesions. These diseases may also lead to fistula formation (deep ulcers of the intestine or rectum) and intestinal blockage. In the United States alone, these diseases affect an estimated 500,000 to 1,000,000 patients per year.

There are few drugs or other modes of treatment available that effectively treat or prevent chronic gastrointestinal disorders. Currently, the medical management of Inflammatory Bowel Disease and related conditions includes a broad-spectrum of antibiotics, steroids, and immune modulating therapies such as cyclosporine. In addition, drugs such as aminosalicylates (e.g., mesalamine and olsalazine) can be prescribed, but NSAIDs are contraindicated because they exacerbate gastrointestinal inflammation in Inflammatory Bowel Disease patients. Patients who fail to respond to drug treatment may be candidates for surgical intervention. However, surgery is a dangerous procedure that causes major discomfort, great expense, and usually an extended hospital stay. Further, surgery always involves the risk of mortality. Unfortunately, for many sufferers, medical management does not completely eliminate their chronic gastrointestinal disorders.

There is, accordingly, a need for a simple, effective treatment that can alleviate and prevent NSAID-induced gastrointestinal damage and chronic gastrointestinal disorders, without the complication of side effects.

SUMMARY OF THE INVENTION

The invention is a method of preventing, countering or reducing chronic gastrointestinal disorders or NSAID-induced gastrointestinal damage in a subject, which comprises:

A. hyperimmunizing an egg-producing animal or a milk-producing animal; and

B. administering to the subject an effective amount of hyperimmunized egg product, hyperimmunized milk product, or combinations thereof.

In another embodiment, the invention is a method of preventing, countering, or reducing inflammation in a subject which comprises simultaneously administering an effective amount of an NSAID to the subject and an effective amount of a product selected from the group consisting of hyperimmunized egg product, hyperimmunized milk product, and combinations thereof.

In still another embodiment, the invention is a method of preventing, countering or reducing chronic gastrointestinal disorders or NSAID-induced gastrointestinal damage in a subject, which comprises separately administering an effective amount of a hyperimmunized egg product and a hyperimmunized milk product to the subject.

DESCRIPTION OF THE INVENTION

The invention relates to a method for significantly reducing or preventing the formation of ulcerations in the gastrointestinal tract by using a natural food product, i.e., hyperimmunized egg and/or hyperimmunized milk. The following definitions apply throughout:

Definitions

The term "hyperimmunized egg product" means whole egg or products derived therefrom, obtained from egg-producing animals maintained in a hyperimmune state.

The term "hyperimmunized milk product" means milk or products derived therefrom, obtained from milk-producing animals maintained in a hyperimmune state.

The term "processed hyperimmunized egg product" means hyperimmunized egg product which is in an acceptable form for administration to a subject.

The term "processed hyperimmunized milk product" means hyperimmunized milk product which is in an acceptable form for administration to a subject.

The term "inflammation" means the involvement of a complex series of events that include dilation of blood vessels along with increased permeability and blood flow, exudation of fluids, including plasma proteins, change in cell mediator levels, and leukocyte migration into the inflammatory focus. Inflammation of the intestine may also be associated with sloughing of mucous membranes, ulceration, and perforation.

The term "chronic" means of long duration, continuing, prolonged, or lingering.

The term "gastrointestinal disorder" means the disturbance or derangement of the regular or normal physical function or vitality of the gastrointestinal system. Some examples include Crohn's Disease and ulcerative colitis, among others.

The term "gastrointestinal damage" means the impairment or harm of the regular or normal physical function or vitality of the gastrointestinal system. Some examples include single or multiple ulcerations, lesions and bleeding, among others.

The term "administer" means any method of providing a subject with a substance, including orally, intranasally, parenterally (intravenously, intramuscularly, or subcutaneously) or rectally.

The term "subject" means any living animal that has a gastrointestinal system and is subject to gastrointestinal disorders and/or damage, including humans and other animals.

The method relates particularly to the use of hyperimmunized egg or hyperimmunized milk, each of which are natural food products. As such, although the risk of allergic reaction is always present, these natural food products can be used to treat chronic gastrointestinal disorders as well as NSAID-induced gastrointestinal disorders, without the fear of side effects. For purposes of this invention, treating includes preventing, countering or reducing.

Some symptoms of chronic gastrointestinal disorders and NSAID-induced gastrointestinal damage that can be treated by the method of this invention are: inflammatory foci, ulcerations, bleeding and perforations.

NSAIDs are generally used for treating joint related inflammatory diseases such as rheumatoid arthritis, osteoarthritis, ankylosing spondylitis, bursitis, and tendinitis, and may also be effective in treating other diseases that may be associated with inflammation, such as Alzheimer's disease, multiple sclerosis and Parkinson's disease.

The method of this invention enhances the ability of sufferers of such inflammatory diseaseses to use NSAIDs with less of a concern for the damaging gastrointestinal side effects of this category of drug. If a subject will be placed on a regimen of NSAID treatment, that subject can be pretreated by the method of this invention for some time prior to taking the NSAIDs. Further, the method of this invention can be undertaken concurrently with NSAID treatment to prevent, counter, or reduce the gastrointestinal damaging side effects of such treatment.

An added benefit of using this method is that those who use the hyperimmunized egg and/or milk product are able to be administered, or treated, with higher dosages of NSAIDs to produce a greater anti-inflammatory effect.

A subject suffering from NSAID-induced and other gastrointestinal disorders and damage can be treated by any of the following procedures: administering hyperimmunized egg product alone; administering hyperimmunized milk product alone; or administering both hyperimmunized egg product and hyperimmunized milk product to the subject.

Hyperimmunized Egg Product

The hyperimmunized egg product can be produced by any egg-producing animal. It is preferred that the animal be a member of the class Aves. Within the class Aves, domesticated fowl are preferred, but other members of this class, such as turkeys, ducks, and geese, are a suitable source of hyperimmunized egg product.

When such egg-producing animals are brought to a specific state of immunization by means of, for example, periodic booster administrations of antigens, the animals will produce eggs that, when consumed by a subject, will have beneficial properties in the treatment of NSAID-induced damage and chronic gastrointestinal disorders in that subject.

The beneficial egg properties arc not produced by all egg-producing animals that are simply immunized. The induction of immune sensitivity alone (such as chickens immunized against fowl diseases) is insufficient to cause the above-mentioned beneficial properties in eggs. It is only in the hyperimmune state that the eggs produced have the desired effect. This special state is preferably achieved by administering periodic boosters to the egg-producing animal with sufficiently high dosages of antigens. The preferred dosage range should be equal to or greater than 50% of the dosage necessary to cause a primary immune response in the egg-producing animal. Having knowledge of the requirement for developing and maintaining a hyperimmune state, it is within the skill of the art to vary the amount of antigen administered, depending on the egg-producing animal genera and strain employed, in order to maintain the animal in the hyperimmune state.

Alternate modes of hyperimmunizing egg producing animals can be used in place of antigenic vaccines and include the use of genetic vaccines. In particular, any DNA construct (generally consisting of a promoter region and an antigen encoding sequence) will trigger antibody release. Genetic vaccines consist of antigen-coding vectors, fragments of naked DNA, plasmid DNA, DNA-RNA antigens, DNA-protein conjugates, DNA-liposome conjugates, DNA expression libraries, and viral and bacterial DNA delivered to produce an immune response. Methods of DNA delivery include particle bombardment, direct injection, viral vectors, liposomes and jet injection, among others. When applying these delivery methods, much smaller quantities are necessary and generally result in more persistent antigen production. When using such genetic processes, the preferred method for introducing DNA into avians is through intramuscular injection of the DNA into the breast muscle.

The following is an example of the procedure used to bring an egg-producing animal to a heightened state of immunity and administering the hyperimmunized egg product to the subject:

1. Selecting one or more antigens.
2. Eliciting an immune response in the egg-producing animal by primary immunization.

3. Administering booster vaccines of antigens of appropriate dosage to induce and maintain the hyperimmune state.
4. Collecting and processing the eggs to produce a hyperimmunized egg product from the egg-producing animal maintained in the hyperimmune state.
5. Administering the hyperimmunized egg product to the subject.

Step 1

Any antigen or combination of antigens may be employed. The antigens can be bacterial, viral, protozoan, fungal, cellular, or any other substances to which the immune system of an egg-producing animal will respond. The critical point in this step is that the antigen(s) must be capable of inducing immune and hyperimmune states in the egg-producing animal. One preferred vaccine is a mixture of polyvalent bacterial antigens, referred to as Series 100 (S-100) vaccine. The bacteria included in the S-100 vaccine are listed in table 1 of Example 1. This vaccine has been previously described in U.S. Pat. Nos. 5,106,618 and 5,215,746, both assigned to Stolle Research and Development Corporation. Another preferred vaccine for use is the EB-100E vaccine, the details of which are also described in Example 1.

Step 2

The vaccine can be either a killed or live-attenuated vaccine and can be administered by any method that elicits an immune response. It is preferred that immunization be accomplished by administering the antigens through intramuscular injection. The preferred muscle for injection in an avian is the breast muscle. Dosage is preferably 0.5–5 milligrams of the antigen(s) vaccine. Other methods of administration that can be used include intravenous injection, intraperitoneal injection, rectal suppository, or oral administration. When DNA techniques are used for the hyperimmunization process, much smaller quantities are required, generally 1–100 micrograms.

It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. In general, the appearance of egg antibodies after immunization with the vaccine is indicative of an immune response. The minimum dosage of antigen necessary to induce an immune response depends on the vaccination procedure used, including the type of antigen(s) used as well as the type of egg-producing animal used as the host.

Step 3

The hyperimmune state is preferably induced and maintained by repeated booster administrations of an appropriate dosage at fixed time intervals. The time intervals are preferably two-week intervals over a period of six months. However, it is essential that the booster administrations do not lead to immune tolerance.

It is possible to use other hyperimmunization maintenance procedures or combination of procedures, such as, for example, intramuscular injection for primary immunization and intravenous injection for booster injections. Further procedures include simultaneously administering microencapsulated and liquid antigen, or intramuscular injection for primary immunization, and booster dosages by oral administration or parenteral administration by microencapsulation means.

Several combinations of primary and hyperimmunization are known to those skilled in the art.

Step 4

The hyperimmunized eggs can be processed for administration to the subject in a variety of ways. These include therapeutic administration of the hyperimmunized egg product itself (e.g., capsules) and incorporation of the hyperimmunized egg product into foods.

It is preferred that the egg product be incorporated into a food product. One preferred method for preparing the egg to be incorporated into a food product involves drying the egg into an egg powder. Although various methods are known for drying eggs, spray drying is a preferred method. A temperature of below 140° F. (60° C.) is preferably used. Samples are monitered for moisture content during the drying process to obtain a final product having any consistency desired. The dried egg powder can be used in drinks in the form of, for example, protein powders, power building drinks, protein supplements and any other nutritional, athlete-associated products. In addition, the egg powder can be used in bake mixes, power bars, candies, cookies, etc. Other examples of egg processing include making an omelette, soft or hard-boiling the egg, baking the egg, or, if desired, the egg can be eaten raw.

Finally, it is generally known in the art that the yolk and/or white fractions contain the agent or agents responsible for the beneficial properties observed and referred to above. Those having ordinary skill in the art would clearly recognize that further separation could provide more potent fractions.

Step 5

In the case of treating chronic gastrointestinal disorders, the hyperimmunized egg product should be administered to the subject in an amount that is immunologically effective in treating the particular disorder.

In cases where the subject is taking or is preparing to take NSAIDs for the treatment of inflammation, the procedure is different. For those who have not yet begun the NSAID treatment, it is preferred that those subjects be pre-treated for 6–8 weeks with the hyperimmunized egg product. After pre-treatment with the hyperimmunized egg product, the subject should continue to be administered hyperimmunized egg product along with the administration of the NSAID for treating inflammation. Daily dosages are preferred.

For those taking NSAIDs, pretreatment with, or concurrent administration of, hyperimmunized egg product will reduce the incidence of gastrointestinal damage. As such, higher dosages of NSAIDs can be administered without the fear of increased gastrointestinal damaging, side effects.

Duration and intensity of the treatment will depend on the particular condition and the advancement of the condition of the subject. The hyperimmunized egg product can be provided in any amount that treats or prevents NSAID-induced or chronic gastrointestinal damage and disorders. For example, in some cases, daily amounts of one or more whole, hyperimmunized eggs, or hyperimmunized egg products containing the equivalent of one or more whole, hyperimmunized eggs, can be administered to the subject depending on the particular circumstance of the gastrointestinal damage or disorder.

The hyperimmunized egg product produced by hyperimmunizing an avian with certain antigens, is effective in treating chronic gastrointestinal disorders as well as NSAID-induced gastrointestinal damage. The preferred antigen mixture injected into the avians does not contain specific antigens which are known to cause gastrointestinal damage. Therefore, it is surprising that treatment with the egg product obtained from avians immunized against a mixed antigen vaccine is effective in reducing and preventing chronic and NSAID-induced gastrointestinal damage when administered to a subject.

Hyperimmunized Milk Product

The source of the milk includes any milk-producing animal. In a preferred embodiment, any bovid animal is used. Dairy cows are preferred, but any other bovids or animals that produce milk in commercially feasible quantities, such as goats, sheep, buffalo or llamas can also be used.

This hyperimmunized milk product can be used in preventing, countering or reducing chronic and NSAID-induced gastrointestinal disorders in a subject. When such milk-producing animals are brought to a specific state of immunization by means of, for example, periodic booster administrations of antigens, the milk-producing animal will produce milk that, when administered to a subject, will have beneficial properties in the treatment of chronic and NSAID-induced gastrointestinal damage in that subject.

All the modes and alternative modes of immunization and administration described for the egg-producing animals in producing hyperimmunized egg product can be utilized in milk-producing animals for producing the hyperimmunized milk and administering the hyperimmunized milk to a subject.

The following is an example of the procedures used to bring a milk-producing animal to a state of immunity and administering the hyperimmunized milk product to the subject:

1. Selecting of one or more antigens.
2. Eliciting an immune response in the milk-producing animal by primary immunization.
3. Administering booster vaccines of antigens of appropriate dosage to induce and maintain the hyperimmune state.
4. Collecting and processing milk to produce a hyperimmunized milk product from the milk-producing animal maintained in the hyperimmune state.
5. Administering the hyperimmunized milk to the subject.

Step 1

This step is performed in the same manner as described in step 1 above for the hyperimmunized egg. The only difference is that the antigen or combination of antigens must elicit a response in a milk-producing animal.

Step 2

The vaccine can be either killed or live attenuated vaccine and can be administered by any method that elicits an immune response. In one method, a vaccine composed of antigen derived from $1 \times 10^6$ to $1 \times 10^{20}$, preferably $10^8$ to $10^{10}$, most preferably $2 \times 10^8$, killed bacterial cells is administered by intramuscular injection. However, other methods such as intravenous injection, intraperitoneal injection, rectal suppository, or oral administration may be used.

In cases wherein DNA techniques are used for the hyperimmunization process, much smaller quantities are required, preferably 1–100 micrograms.

It can be determined whether the vaccine has elicited an immune response in the milk-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. In general, the appearance of milk antibodies after immunization with the vaccine is indicative of an immune response. The minimum dosage of antigen necessary to induce an immune response depends on the vaccination procedure used, including the type of antigen(s) used as well as the type of milk-producing animal used as the host.

The hyperimmune state is preferably induced and maintained by repeated booster administrations of an appropriate dosage at fixed time intervals. The time intervals are preferably two-week intervals over a period of six months. It is essential that the booster administrations do not lead to immune tolerance.

In a preferred embodiment, hyperimmunization of milk-producing animals may be achieved by a single administration of microencapsulated vaccine, prepared as described in U.S. Pat. No. 5,352,462. The advantage of the controlled release form of hyperimmunization is that the constant exposure to the antigen ensures that the animal remains in the hyperimmune state.

It is possible to use other hyperimmunization maintenance procedures or a combination of procedures, such as intramuscular injection for primary immunization and intravenous injection for booster injections. Further procedures include simultaneously administering microencapsulated and liquid antigen, or intramuscular injection for primary immunization, and booster dosages by oral administration or parenteral administration by microencapsulation means. Several combinations of primary and hyperimmunization are known to those skilled in the art. Step 4

The hyperimmunized milk can be collected by conventional methods, then pasteurized. Following pasteurization, the fat is removed by standard procedures and the milk is spray dried by conventional spray drying procedures known in the art. Fluid milk can also be used as concentrated milk products or a fraction of the milk, such as the acid whey fraction, having the beneficial properties.

The fat-free milk can be incorporated into any food product. For example, puddings or yogurt may be prepared with the hyperimmunized milk product. In addition, when the fat-free milk is treated with acid at about room temperature (bringing the pH of the milk to about 4.2–4.6) and the casein is separated after precipitation thereof, the acid whey supernatant fraction can also be added to syrups, ice-cream mixes, candy, beverages, cattle feeds or the like.

In the case of treating chronic gastrointestinal disorders, the hyperimmunized milk product should be administered to the subject in an amount that is immunologically effective in treating the particular disorder.

In cases where the subject is taking or is preparing to take NSAIDs for the treatment of inflammation, the procedure is different. For those who have not yet begun the NSAID treatment, it is preferred that those subjects be pre-treated for 6–8 weeks with the hyperimmunized milk product. After pre-treatment with the hyperimmunized milk product, the subject should continue to be administered hyperimmunized milk product along with the administration of the NSAID for treating inflammation. Daily dosages are preferred.

For those who are taking NSAIDs, pretreatment with, or concurrent administration of, hyperimmunized milk product will reduce the incidents of gastrointestinal damage. As such, higher dosages of NSAIDs will be able to be administered without the fear of increased gastrointestinal damaging side effects.

Duration and intensity of the treatment will depend on the particular condition and the advancement of the condition of the subject. The hyperimmunized milk product can be provided in any amount which treats or prevents NSAID-induced or chronic gastrointestinal damage and disorders. For example, in some cases, daily amounts of 1mL to 10 L based on fluid milk can be administered to the subject depending on the particular circumstance of the gastrointestinal damage or disorder.

Both Hyperimmunized Egg and Hyperimmunized Milk

In another embodiment, a combination of both a hyperimmunized egg product and a hyperimmunized milk product may be administered to the subject.

The hyperimmunized egg product and hyperimmunized milk product are prepared by the methods as described above. In particular, each product is processed into an appropriate form for administration according to the methods outlined above.

With regard to the administration of both hyperimmunized egg product and hyperimmunized milk product, in one embodiment the hyperimmunized egg product and hyperimmunized milk product can be separately administered to the subject. In an alternate embodiment, the subject can be administered a composition comprising an effective amount of hyperimmunized egg product and hyperimmunized milk product.

The administration to the subject should be carried out in an amount that is effective for treating the chronic gastrointestinal disorder or NSAID-induced gastrointestinal damage. It is preferred that an amount of the processed hyperimmunized egg product be administered, or mixed, with an equal amount of hyperimmunized milk product prior to administration. However, if, for example, better treatment and prevention are observed when the subject is administered a higher dosage of the hyperimmunized egg administered, or mixed, with a lower dosage of hyperimmunized milk, or vice versa, then such unequal dosages are appropriate for treatment and prevention, and should be administered in those amounts. In addition, it is believed that there is a possible synergistic effect of the combined hyperimmunized egg and milk product. As such, administration should be adjusted accordingly. Those having skill in the art are familiar with determining dosage amounts that will best treat and prevent the disorder or damage of interest. The hyperimmunized egg product and the hyperimmunized milk product can each be processed into any form, as described above, for administration to the subject.

The administration of both the hyperimmunized egg and milk products can be provided in any amount that treats or prevents NSAID-induced or chronic gastrointestinal damage or disorder. Treatment is administered as described above for the hyperimmunized egg alone and the hyperimmunized milk alone. Duration and intensity of the treatment will depend on the particular condition and the advancement of the subject's condition.

The advantageous properties of this invention can be observed by reference to the following examples which illustrate the invention.

EXAMPLES

Example 1

This example illustrates the cytoprotective effect of the hyperimmunized egg on gastrointestinal damage induced by the NSAID indomethacin.

Preparation of S-100 Vaccine

A bacterial culture containing the spectrum of bacteria shown in Table 1 below, as obtained from the American Type Culture Collection, was reconstituted with 15 ml, of media and incubated overnight at 37° C. Once good growth was obtained, approximately one-half of the bacterial suspension was employed to inoculate one liter of broth with the inoculate being incubated at 37° C.

After good growth was visible in the culture, the bacterial cells were harvested by centrifugation of the suspension for 20 minutes to remove the media. The bacterial pellet obtained was resuspended in sterile saline solution and the bacterial sample was centrifuged three times to wash the media from the cells. After the third sterile saline wash, the bacterial pellet was resuspended in a small amount of double distilled water.

The media-free bacterial suspension was killed by placing the suspension in a glass flask in an 80° C. water bath overnight. The viability if the broth culture was tested with a small amount of killed bacteria, incubated at 37° C. for five days and checked daily for growth to certify that the bacteria had been killed.

The killed bacteria were lyophilized until dry. The dry bacteria were then mixed with sterile saline solution to a concentration of $2.2 \times 10^8$ bacterial cells/mL saline (1.0 optical density reading at 660 nm). Bacteria contained in S-100 vaccine are listed in Table 1 below.

TABLE 1

| S-100 Bacterial List | |
|---|---|
| Escherichia coli | Escherichia coli (Aerobacter) |
| Klebsiella pneumoniae | Pseudomonas aeruginosa |
| Salmonella typhimurium | Salmonella dysenteriae |
| Salmonella enteriditis | Salmonella epidermis |
| Salmonella simulans | Streptococcus pyogenes, type 1 |
| Streptococcus pyogenes, type 3 | Streptococcus pyogenes, type 5 |
| Streptococcus pyogenes, type 8 | Streptococcus pyogenes, type 12 |
| Streptococcus pyogenes, type 14 | Streptococcus pyogenes, type 18 |
| Streptococcus pyogenes, type 22 | Pseudomonas vulgaris |
| Streptococcus agalactiae | Streptococcus mitis |
| Streptococcus mutans | Streptococcus salavarius |
| Streptococcus sanguis | Streptococcus pneumoniae |
| Propionibacterium acnes | Haemophilis influenzae |

EB -100E Vaccine

The EB-100E vaccine is known by the trade name of Scourmune®-CRT, manufactured by Schering-Plough Animal Health, of Kenilworth, N.J., USA. The vaccine consists of *Clostridium perfringens*, type C, *Escherichia coli*, porcine rotavirus, and transmissible g stroenteritis.

Immunization Procedure for Hyperimmunized Egg Product

A killed preparation of pathogens was prepared as described above. For the first vaccination, the bacteria were mixed with complete Freund's adjuvant, and 5.6 mg of bacterial material was injected into the breast muscle of a chicken. For the remaining vaccines, the bacterial preparation was mixed with incomplete Freund's adjuvant and injected into the chickens at two week intervals for six months.

Immunization Procedure for Hyperimmunized Milk Product

The hyperimmunized milk-product used in this example was obtained from the Stolle Research & Development Corporation (Stolle), Cincinnati, Ohio, USA, batch Nos. 247A5 and 289A5. Stolle has prepared hyperimmunized milk product by the following immunization process.

A killed preparation of pathogens was prepared in the manner described above. The polyvalent antigen sample (S-100) obtained was microencapsulated by a conventional phase-separation process to prepare a polyvalent antigen-containing microparticle product. Generally, the antigen-containing shaped matrix materials are formed from polymers of biocompatible material, preferably biodegradable or bioerodable materials, preferably polyactic acid, polyglycolic acid, copolymers of lactic and glycolic acids, polycaprolactone, copolyoxalates, proteins such as collagen, fatty acid esters of glycerol, and cellulose esters. These polymers are well known in the art. The polymeric matrix material employed was a biodegradable lactide-glycolide copolymer.

Killed pathogens are encapsulated in such matrix materials, preferably as microspheres of between 1–500 μm diameter, preferably 10–250 μm. The encapsulation processes are conventional and comprise phase separation methods, interfacial reactions, and physical methods. Many combinations of matrices and many concentrations of assorted antigens may be employed, in order to provide for optimal rates of release of bacterial antigens to the host body from the microparticles. These combinations can be determined by those skilled in the art without undue experimentation.

The microparticles in the example were less than 250 μm in diameter. Approximately 750 mg of microparticles containing 22% (16.5 mg) of polyvalent antigen was then suspended in about 3 cc of a vehicle (1 wt. % Tween® 20 and 2 wt. % carboxymethyl cellulose in water).

A small group of cattle was selected from a larger herd of cattle. Five of these randomly selected cattle were selected as controls. Four cows were injected intramuscularly with microparticles containing polyvalent antigen. Microparticle samples were sterilized with 2.0 mRad of gamma radiation. Antibody (gG) titer levels were determined periodically from samples of cow's milk obtained from the inoculated cows, as well as from the control cows.

Administration of the Hyperimmunized Egg and Hyperimmunized Milk Products to the Subjects Seven groups of six female albino rats, weighing approximately 200 grams each, were fed various diets for a period of approximately seven weeks. The diets were as follows:

Group 1—Control-basal diet of certified meal. (Certified Rodent Chow 5001, manufactured by Purina Mills.)

Group 2—10% Hyperimmunized Egg (S-100 vaccine)—in powdered form, by weight of feed.

Group 3—10% Hyperimmunized Egg (EB-100E vaccine)—in powdered form, by weight of feed.

Group 4—10% Hyperimmunized Milk (S-100 vaccine)—in powdered form, by weight of feed.

Group 5—10% Hyperimmunized Egg (S-100 vaccine)+10% Hyperimmunized Milk (S-100 vaccine)—in powdered form, by weight of feed.

Group 6—10% Hyperimmunized Egg (EB-100E vaccine)+10% Hyperimmunized Milk (S-100 vaccine)—in powdered form, by weight of feed.

The rats were allowed free access to food and water and were maintained on these diets for about seven weeks. Forty-eight hours prior to sacrifice, all rats were dosed with 15 mg/kg of indomethacin by gavage, prepared as a 1.5% w/v suspension in methylcellulose solution. Upon sacrifice, the intestines were removed and scored for the presence of lesions (Table 2).

TABLE 2

Method of Scoring Lesions

| Score | Appearance of Intestines |
|---|---|
| 0 | no lesions, normal appearance |
| 1 | 1–5 distinct lesions; no adhesions or perforations of intestinal wall |
| 2 | 6–10 distinct lesions; no adhesions or perforations of intestinal wall |
| 3 | 10 distinct lesions; no adhesions or perforations of intestinal wall |
| 4 | 10 distinct lesions; one or more perforations of intestinal wall |
| 5 | one or more perforations, no mortality |
| 6 | one or more perforations producing death (no deaths were seen in any group) |

The scores for the rats are detailed in Table 3. Two independent evaluations were made of the lesions and averaged into a mean lesion value. It is these mean lesion values that are scored in Table 3

TABLE 3

Scoring of Lesions

| Group No. | Diet | Ulcer Score (Mean Lesion Value) | p value* |
|---|---|---|---|
| 1 | Certified meal (Control) | 2.8 | |
| 2 | HIE 10% (S 100) | 1.3 | <.05 |
| 3 | HIE 10% (EB 100E) | 1.3 | <.05 |
| 4 | HIM 10% | 1.5 | <.05 |
| 5 | HIE 10% (S 100) + HIM 10% | 0.8 | <.05 |
| 6 | HIE 10% (EB 100E) + HIM 10% | 0.6 | <.05 |

*Duncan's Multiple Range Test Analysis of Variance
HIE = hyperimmunized egg product
HIM = hyperimmunized milk product The above scores were based solely upon the quantitative nature of the lesions. The lesion scores illustrate the cytoprotective effect and alleviation of the cytodestructive effect by the hyperimmunized egg product when fed to the rats before they were dosed with indomethacin. These data indicate that pretreatment with hyperimmunized egg product, hyperimmunized milk product, or a combination of both, significantly reduces NSAID-induced damage of the intestine. The data would imply that patients requiring NSAID treatment for chronic inflammatory conditions such as arthritis, could use hyperimmunized egg product, hyperimmunized milk product, or a combination of the two along with their usual dosage of NSAID and experience a reduction in the typical NSAID-induced gastrointestinal side effects. Additionally, the use of the hyperimmunized egg and milk products in conjunction with NSAIDs could permit an increase in the prescribed NSAID dosage thereby enhancing its therapeutic effect without increasing the risk of its detrimental side effects.

Example 2

This example examines and illustrates the severity of the lesions induced by indomethacin and the cytoprotective effect of the hyperimmunized egg and hyperimmunized milk as prepared in Example 1. The protocol used was the same as Example 1, except that the rats were fed the various diets for about ten weeks before they were dosed with indomethacin and subsequently sacrificed. Upon sacrifice, the intestines were removed and scored for the presence of lesions as outlined in Table 4 below.

TABLE 4

Method of Scoring Lesions

| Score | Appearance of Intestines |
|---|---|
| 0 | no lesions, normal appearance |
| 1 | 1–2 distinct circular lesions |
| 2 | 3–5 distinct circular lesions |
| 3 | 10 distinct lesions; no adhesions or perforations of intestinal wall |
| 4 | 11–15 distinct circular lesions |
| 5 | 16–20 distinct circular lesions |
| 6 | 20 distinct circular lesions |
| 7 | one or more linear hemorrhagic lesions 5 mm |
| 8 | one or more linear hemorrhagic lesions 5 mm |
| 9 | one or more adhesions |
| 10 | one or more perforations |

The scores for the rats are detailed in Table 5. The mean lesion value is the average score among the groups.

TABLE 5

Scoring of Lesions

| Group No. | Diet | Ulcer Score (Mean Lesions Value) | p value* |
|---|---|---|---|
| 1 | Certified meal (Control) | 9.0 | |
| 2 | HIE 10% (S 100) | 3.8 | <.05 |
| 3 | HIE 10% (EB 100E) | 2.8 | <.05 |
| 4 | HIM 10% | 7.2 | <.05 |
| 5 | HIE 10% (S 100) + HIM 10% | 5.7 | <.05 |
| 6 | HIE 10% (EB 100E) + HIM 10% | 3.0 | <.05 |

*Duncan's Multiple Range Test Analysis of Variance
HIE = hyperimmunized egg product
HIM = hyperimmunized milk product The above scores were based upon a more detailed scoring system than that used in Example 1. Both quantitative and qualitative parameters were employed (i.e., appearance of lesions and the severity of the lesions). A comparison of Example 2 with Example 1 shows that pretreatment with hyperimmunized egg product provided a higher level of protection in Example 2 than Example 1.

The scores illustrate the cytoprotective effect and alleviation of the cytodestructive effect by the hyperimmunized egg product when fed to the rats before they were dosed with indomethacin. In particular, the greatest protection from lesion formation occurred when the combination of hyperimmunized egg and hyperimmunized milk was used. In addition, the EB-100E vaccine seems to have a greater effect on reducing the cytodestructive effect of the indomethacin than the S-100 vaccine.

Example 2 confirms that long-term ingestion of hyperimmunized egg and/or hyperimmunized milk protects against indomethacin-induced intestinal ulceration. The studies support the concept that the hyperimmunized egg and milk products have a cytoprotective effect capable of reducing NSAID-induced gastrointestinal adverse effects. Concomitantly, the use of hyperimmunized egg product, hyperimmunized milk product, or a combination of the two products may permit therapeutic use of higher dosages of NSAIDS.

We claim:

1. A method for preventing or reducing non-steroidal, anti-inflammatory drug-induced gastrointestinal damage in a subject who will receive or is receiving a non-steroidal, anti-inflammatory drug, comprising the steps of:

hyperimmunizing an egg-producing animal or a milk-producing animal;

collecting hyperimmunized egg product or hyperimmunized milk product from the hyperimmunized animal;

administering the egg or milk product to the subject, wherein the egg or milk product is capable of preventing or reducing said gastrointestinal damage, in an amount sufficient to prevent or reduce said gastrointestinal damage; and administering a non-steroidal, anti-inflammatory drug.

2. The method of claim 1 wherein the subject is administered an effective amount of hyperimmunized egg product.

3. The method of claim 1 wherein the subject is administered an effective amount of hyperimmunized milk product.

4. The method of claim 1 wherein the subject is separately administered an effective amount of hyperimmunized egg product and hyperimmunized milk product.

5. The method of claim 1 wherein the subject is administered a composition comprising an effective amount of hyperimmunized egg product and hyperimmunized milk product.

6. The method of claim 1 wherein the egg-producing animal or milk-producing animal is hyperimmunized with an antigenic or genetic vaccine.

7. The method of claim 6 wherein the antigenic vaccine comprises at least one antigen selected from the group consisting of bacterial, viral, protozoan, fungal, and cellular antigens and combinations thereof.

8. The method of claim 6 wherein the genetic vaccine comprises at least one antigen coding DNA construct selected from the group consisting of fragments of naked DNA, plasmid DNA, viral DNA, bacterial DNA, DNA expression libraries, DNA-RNA antigens, DNA-protein conjugates and DNA liposome conjugates, and combinations thereof.

9. The method of claim 1 wherein the egg-producing animal is a member of the avian class.

10. The method of claim 9 wherein the egg-producing animal is selected from the group consisting of fowl, turkey, duck, and goose.

11. The method of claim 1 wherein the milk-producing animal is a member of the bovid class.

12. The method of claim 11 wherein the milk-producing animal is selected from the group consisting of cow, goat, sheep, buffalo, and llama.

13. The method of claim 6 wherein the antigenic vaccine is a killed vaccine.

14. The method of claim 6 wherein the antigenic vaccine is a live-attenuated vaccine.

* * * * *